(12) United States Patent
Slim et al.

(10) Patent No.: US 6,379,709 B1
(45) Date of Patent: Apr. 30, 2002

(54) ANGIOGENESIS INHIBITORS AND ACTIVATORS FROM SHARK CARTILAGE

(75) Inventors: George Charles Slim; Paul Frank Davis; Yi He; Bei Xu, all of Wellington (NZ)

(73) Assignees: Industrial Research Limited, Auckland; University of Otago, Dunedin, both of (NZ)

(*) Notice: Subject to any disclaimer, the term of this patent is extended or adjusted under 35 U.S.C. 154(b) by 0 days.

(21) Appl. No.: 09/367,727

(22) PCT Filed: Feb. 19, 1998

(86) PCT No.: PCT/NZ98/00021

§ 371 Date: Dec. 10, 1999

§ 102(e) Date: Dec. 10, 1999

(87) PCT Pub. No.: WO98/36760

PCT Pub. Date: Aug. 27, 1998

(30) Foreign Application Priority Data

Feb. 20, 1997 (NZ) .................................................. 314274

(51) Int. Cl.[7] .......................... A61K 35/34; C07K 1/100
(52) U.S. Cl. .......................... 424/548; 514/21; 530/400
(58) Field of Search .......................... 424/548; 514/21, 514/859, 863; 530/400

(56) References Cited

U.S. PATENT DOCUMENTS

| | | |
|---|---|---|
| 3,400,199 A | 9/1968 | Balassa |
| 3,966,908 A | 6/1976 | Balassa |
| 4,444,752 A | 4/1984 | Prudden |
| 4,473,551 A | 9/1984 | Schinitsky |
| 4,656,137 A | 4/1987 | Balassa |
| 4,822,607 A | 4/1989 | Balassa |
| 5,618,925 A | * 4/1997 | Dupont et al. |

FOREIGN PATENT DOCUMENTS

| | | |
|---|---|---|
| WO | PCT/CA95/00233 | 4/1995 |
| WO | PCT/CA95/00617 | 10/1995 |
| WO | PCT/CA96/00549 | 8/1996 |
| WO | WO 96/23512 | * 8/1996 |

OTHER PUBLICATIONS

Macrides et al. Fundamental and Applied Toxicology, 33(1): 31–37. Hepatoprotective effects of the shark bile salt 5beta–scymnol on acetaminophen–induced liver damage in mice, Sep. 1996.*

JAMA, May 3, 1965, vol. 192 No. 5, "Healing with Cartilage" Editorial, p. 411 to 412.

Cancer Letters, 1990, vol. 51, "A novel angiogenic inhibitor derived from Japanese shark cartilage(I). Extraction and estimation of inhibitory activities toward tumor and embryonic angiogenesis" by T. Oikawa et al. pp. 181–186.

* cited by examiner

Primary Examiner—Christopher R. Tate
Assistant Examiner—Michele Flood
(74) Attorney, Agent, or Firm—Merchant & Gould P.C.

(57) ABSTRACT

A process for obtaining an angiogenesis inhibitor and an angiogenesis activator from shark cartilage comprising, as the key step, the aqueous extraction of dried shark cartilage. The angiogenesis inhibitor obtained is more potent than shark cartilage not subjected to the extraction step. The angiogenesis inhibitor is particularly useful for the prevention or treatment of cancer. The angiogenesis activator is particularly useful for stimulating wound healing.

12 Claims, No Drawings

ANGIOGENESIS INHIBITORS AND ACTIVATORS FROM SHARK CARTILAGE

FIELD OF INVENTION

This invention relates to a process for obtaining angiogenesis activators and angiogenesis inhibitors from shark cartilage, the angiogenesis activator and inhibitor products of the process, compositions comprising them, and methods of using them, particularly for the control of biological processes such as wound healing and tumour formation and growth.

BACKGROUND

Angiogenesis (or neovascularization) is the formation of new blood vessels. Many biological processes, over which control is desired, may depend on the activation of angiogenesis or on the inhibition of angiogenesis. For example, as new blood vessel formation is required by solid tumours for growth, angiogenesis inhibition is an attractive strategy for the treatment of cancer. It has been demonstrated that cartilage extracts inhibit angiogenesis when implanted adjacent to tumours.

Furthermore, the oral consumption of dried powdered shark cartilage has been widely promoted as a natural health remedy for the treatment of cancer. Powdered whole cartilage from bovine trachea and soluble bovine cartilage extracts have also been used to treat a variety of diseases which involve angiogenesis, such as psoriasis and rheumatoid arthritis.

It is known that shark cartilage is comprised principally of calcium salts, protein and polysaccharide material. It is further known that a substantial portion of the polysaccharide material is in the form of glycosaminoglycans (GAGs). The principal GAG in cartilage is chondroitin sulphate.

It has been disputed whether any angiogenesis controlling component of shark cartilage can cross the gut lining of an animal following oral ingestion. It is thought that most of the protein found in shark cartilage would be digested into smaller peptides in the gut. However, GAGs present in cartilage have been shown to be absorbed from the gut largely intact when orally ingested.

Previous studies linking cartilage with the control of angiogenesis have been concerned with angiogenesis inhibition. However, activation of angiogenesis also has therapeutic potential. For example, the promotion of angiogenesis is desirable for expediting biological processes such as wound healing, collateral circulation, and organ transplantation.

It is known to prepare an angiogenesis inhibiting substance from "wet" shark cartilage by extracting it with water to give a solid residue and a lyophilisate. Cartilage described as "wet" is not treated, for example by lyophilisation, to remove water. The solid residue and the lyophilisate were both found to exhibit angiogenesis inhibition.

In addition, there is some evidence that consumption of shark cartilage prepared by conventional processes, especially long term consumption, may cause liver damage. One or more hepatotoxic substances may be present in such cartilage.

SUMMARY OF INVENTION

It is therefore an object of this invention to enable improved control of angiogenesis or to at least provide a useful alternative to known angiogenesis inhibitors and activators by providing a process for obtaining an angiogenesis activator and an angiogenesis inhibitor from dried shark cartilage.

According to first aspect of this invention, there is provided a process for obtaining an angiogenesis activating product and an angiogenesis inhibiting product from shark cartilage comprising the steps of:

drying the shark cartilage so that it is free or substantially free of water, mixing the dried shark cartilage with water to give an aqueous extract and an insoluble residue, and separating the aqueous extract from the insoluble residue, wherein the aqueous extract is an angiogenesis activator and the insoluble residue is an angiogenesis inhibitor.

The water used in the mixing step may contain dissolved salts or electrolytes. For example, it may be a phosphate buffered saline solution. Also, the water may contain one or more water-miscible organic solvents such as ethanol, acetone, or dimethyl sulphoxide, provided to proportion of organic solvent is low, for example, less than 50% v/v, preferably less than 10% v/v.

It is preferred that the shark cartilage is ground, milled, pulverised or powdered to granules having a particle size in the range of less than approximately 500 microns, preferably less than approximately 300 microns.

The separation of the aqueous extract from the insoluble residue may be according to any commonly used separation procedure, for example, filtration including ultrafiltration or dialysis, decantation or centrifugation.

In a preferred embodiment of the invention, the aqueous extract may be dried, for example, via freeze drying, to give a solid product. A solid product may also be obtained from the aqueous extract by the addition of an organic solvent, such as ethanol or acetone, to cause precipitation of a solid followed by filtration and drying.

The shark cartilage may be obtained from one or a mixture of shark species.

In a second aspect of this invention, there is provided an angiogenesis activating product obtained from shark cartilage by a process comprising the steps of:

drying the shark cartilage so that it is free or substantially free of water, mixing the dried shark cartilage with water to give an extract and an insoluble residue, and separating the aqueous extract from the insoluble residue, wherein the aqueous extract is an angiogenesis activator.

In a third aspect of this invention, there is provided an angiogenesis inhibiting product obtained from shark cartilage by a process comprising the steps of:

drying the shark cartilage so that it is free or substantially free of water, mixing the dried shark cartilage with water to give an aqueous extract and an insoluble residue, and separating the aqueous extract from the insoluble residue, wherein the insoluble residue is an angiogenesis inhibitor.

In a preferred embodiment of this aspect of the invention, the insoluble residue exhibits increased angiogenesis inhibition in comparison with the angiogenesis inhibition activity exhibited by the shark cartilage prior to the extraction step.

In a further preferred embodiment of this aspect of the invention, the insoluble residue leads to reduced serum alanine-lactate aminotransferase activity relative to the serum alanine-lactate aminotransferase activity resulting from the use of the shark cartilage not subjected to the extraction step.

In another aspect of this invention, there is provided a composition containing a therapeutically effective amount of an angiogenesis inhibiting product obtained by the process of this invention together with an acceptable carrier.

In a further aspect of this invention, there is provided a composition containing a therapeutically effective amount of an angiogenesis activating product obtained by the process of this invention together with an acceptable carrier.

Yet another aspect of this invention is a method of controlling angiogenesis in an animal comprising administering an effective amount of an angiogenesis activating product obtained by the process of this invention or an angiogenesis inhibiting product obtained by the process of this invention.

In another aspect of this invention, there is provided a use of an angiogenesis activating product or an angiogenesis inhibiting product for the preparation of an agent for controlling angiogenesis.

DETAILED DESCRIPTION

The cartilage used in this invention may be obtained from a mixture of shark species, principally blue shark (*Prionace glauca*), but may include other species such as school shark (*Galeorhinus galeus*), rig or smooth dogfish (*Mustelus lenticulatus*) and spiky dog fish (*Squalus acanthias, Squalus mitsukurii*). The meat adhering to the cartilage may first be removed by any suitable means known to a person skilled in the art such as manual scraping, mild protease treatment or high pressure water treatment. The cartilage may then be dried by freeze drying, air drying or any other suitable means.

The cartilage is preferably milled, ground or pulverised to provide a powder having a particle size of less than approximately 500 microns, preferably less than 300 microns.

The cartilage powder is then suspended in water or in water containing salts or electrolytes such as a phosphate buffered saline solution. The water may contain one or more water miscible organic solvents. However, it is known that the use of a mixture having greater than approximately 50% v/v of an organic solvent results in low yields of products having low activity. Chaotropic salts (those salts which extract proteins) are not desired as their use causes reduced angiogenesis activation of the aqueous extracts.

The amount of cartilage suspended in the water is preferably in the range of between 10 and 50 mg/ml. The suspension is preferably stirred or shaken for a time suitable to enable formation of the desired aqueous extract, preferably up to 3 or 4 days, more preferably approximately 20 hours. During the extraction, the temperature of the suspension is preferably maintained between approximately 4° C. and 50° C. The extraction is typically carried out at a temperature of approximately 18–20° C.

The aqueous extract and the insoluble residue may be separated by any suitable method, for example, centrifugation, decantation or filtration including ultrafiltration or dialysis. The solid residue and the aqueous extract are preferably dried, for example, by freeze drying or air drying, or they may be used directly.

The aqueous extract produced by using shark cartilage that has been cleaned of adhering flesh and minced but not dried does not exhibit angiogenesis activation.

The extract is preferably stored at −18° C. optionally following lyophilisation. After 8 months the angiogenesis activating activity of redissolved extract was approximately 85–90% of the activity of freshly prepared extract.

Each product of the process of this invention (the angiogenesis activator and the angiogenesis inhibitor), may be combined with suitable carriers to provide formulations, such as tablets, capsules, liquids, emulsions, suspensions, creams, ointments, or other formulations, suitable for use as angiogenesis activators or angiogenesis inhibitors.

An angiogenesis inhibitor or an angiogenesis activator of this invention may be administered in any form suitable for the control of angiogenesis such as orally, topically, rectally, intravenously, intraperitoneally, intramuscularly, or by surgical implantation.

The following examples illustrate the invention but are not to be construed as limiting:

EXAMPLE 1

Powdered shark cartilage (100 g) was suspended in water (900 ml). The suspension was shaken for 20 hours at room temperature (18–20° C.). The insoluble residue was then separated from the aqueous extract by filtration. Both the insoluble residue and the aqueous extract was dried.

EXAMPLE 2

Powdered shark cartilage (50 g) was suspended in water (1000 ml). The suspension was stirred at 20° C. for 20 hours. The insoluble residue was then separated from the aqueous extract by centrifugation. Both the insoluble residue and the aqueous extract was dried.

EXAMPLE 3

Powdered shark cartilage was suspended in water (50 mg/ml). The suspension was stirred at 4° C. for 20 hours. The insoluble residue was then separated from the aqueous extract by centrifugation. Both the insoluble residue and the aqueous extract were dried.

EXAMPLE 4

Powdered shark cartilage was suspended in phosphate buffered saline solution (50 mg/ml). The suspension was stirred at 4° C. for 20 hours. The insoluble residue was then separated from the aqueous extract by centrifugation. Both the insoluble residue and the aqueous extract were dried.

EXAMPLE 5

Angiogenesis Assay

The determination of angiogenesis modulatory activity of the fractions involved the development of an assay using rings of rat aorta.

Assay preparation:
- Thoracic aortas were removed from male rats (6–10 weeks of age)
- The excised aortas were transferred immediately to a culture dish containing culture media MCDB131. For all experimental procedures involving MCDB131 the media was supplemented with penicillin (100 U/ml), streptomycin (100 mg/ml) and aminocaproic acid 300 mg/ml.
- The fibroadipose tissue surrounding the aorta was removed carefully with particular attention paid to minimising damage to the aortic wall.
- Rings (1 mm thickness) were sectioned from the aorta and rinsed three times with MCDB131.
- The aortic rings were cultured at 37° C. in 3% $CO_2$, 97% air for 40 min.

Angiogenesis determination:
- The assays were performed using 24 well culture plates (Nune). Each assay was run in triplicate (at least).

In a separate tube 30 ml of thrombin (10 NIH units/ml) was added to MCDB131 (1.5 ml) containing fibrinogen. Following rapid mixing 0.4 ml of the solution was added to each well.

After the gel formation, an aortic ring was placed in the centre of each well.

The rings were then covered with a further 0.4 ml of the fibrinogenthrombin mix.

MCDB131 (1.5 ml) was added to each well.

The aortic rings were cultured at 37° C. in 3% $CO_2$/97% air in a humidified atmosphere.

For analysis of the solid residue, up to approximately 2 mg of shark cartilage or derived material was added to the assay following mixing of the thrombin with fibrinogen. For analysis of the extract, a sample of the extract was added to the assay following mixing of the thrombin with fibrinogen and/or at the time of adding the MCDB131 (1.5 ml) to each well.

The extent of angiogenesis was determined by measuring the area occupied by the new vessels using a microscope with an ocular grid or by taking a photographic record of each well and measuring the area occupied by new vessels using computer image analysis and quantification.

The residue obtained after extraction of the shark cartilage was compared for angiogenesis activity with crude shark cartilage. The experiment was conducted using cartilage from four different commercial sources A to D.

|  | % angiogenesis relative to control | | | |
| --- | --- | --- | --- | --- |
|  | A | B | C | D |
| crude cartilage | 73 | 95 | 95 | 88 |
| residue | 73 | 80 | 76 | 56 |

With the exception of source A, it was found that the residue exhibited a marked increase in angiogenesis inhibition relative to the crude cartilage.

A soluble extract of shark cartilage from a single source was prepared by extraction with water and another by extraction with aqueous MCDB131 medium. By incorporating aliquots of these extracts into the MCDB131 media above the aortic rings, the angiogenesis activity of these extracts was determined at varying concentrations of the extract's dry weight. Analysis of the assay results below showed activation of angiogenesis relative to a control.

|  | concentration (mg/ml) | | | |
| --- | --- | --- | --- | --- |
|  | 0.2 | 0.5 | 1 | 2 |
| water extract | 139 | — | — | 218 |
| MCDB131 extract | 103 | 145 | 158 | 172 |
| (% angiogenesis relative to control) | | | | |

The results show an apparent increasing correlation between concentration of shark cartilage extract and angiogenesis activation.

EXAMPLE 6

ALT Activity

Experimental rats were fed shark cartilage at 6 g/kg of food for 11–12 weeks. Serum from these and from control animals fed a normal diet were assessed biochemically.

The serum alanine-lactate aminotransferase (ALT) activity was found to be increased by a mean of 45% in rats which had been fed shark cartilage not subjected to the process of this invention. For the rats fed the solid residue from the aqueous extraction process of the invention, the increase was only 27%.

ALT is a marker of liver function. Elevated activity is suggestive of liver dysfunction. Long-term consumption of shark cartilage may result in greater elevation of ALT activity indicating increased liver damage. The ALT activity for animals fed the solid residue from the extraction process is reduced. Thus, the extraction process appears to remove one or more hepatotoxic substances from the shark cartilage.

Although the invention has been described by way of example and with reference to embodiments thereof, it should be appreciated that variations and modifications may be made thereto, without the departing from the scope of the claims.

INDUSTRIAL APPLICABILITY

The angiogenesis inhibitor of this invention is useful as a therapeutic agent for the treatment or prevention of diseases or disorders such as cancer where reduced formation of new blood vessels is desired. The angiogenesis activator of the invention is useful as a therapeutic agent where the promotion of new blood vessels is desired, for example, for wound healing.

What is claimed is:

1. A process for obtaining an angiogenesis activating product and an angiogenesis inhibiting product from shark cartilage comprising steps of:

drying the shark cartilage so that it is free of water forming a dried shark cartilage, processing the dried shark cartilage into a particulate, contacting the particulate dried shark cartilage with water to give an aqueous extract and an insoluble residue, and separating the aqueous extract from the insoluble residue comprising the angiogenesis inhibiting product, wherein the aqueous extract is an angiogenesis activator.

2. A process as claimed in claim 1 further comprising the step of obtaining a solid angiogenesis activator from the aqueous extract.

3. A process as claimed in claim 2 wherein the solid angiogenesis activator is obtained by lyophilisation of the aqueous extract.

4. A process as claimed in claim 2 wherein the solid angiogenesis activator is obtained by adding a water miscible organic solvent to the aqueous extract to cause precipitation of a solid and then filtering and drying the solid.

5. A process as claimed in claim 1 wherein the dried shark cartilage is mixed with water containing one or more dissolved salts.

6. A process as claimed in claim 5 wherein the dried shark cartilage is mixed with phosphate buffered saline solution.

7. A process as claimed in claim 1 wherein the dried shark cartilage is ground, milled, pulverised or powdered to granules having a particle size in the range of less than approximately 500 microns.

8. An angiogenesis inhibitor obtained by the process claimed in claim 1.

9. An angiogenesis inhibitor as claimed in claim 8 which exhibits increased angiogensis inhibition in comparison with the angiogenesis inhibition exhibited by shark cartilage prior to the extraction step.

10. An angiogenesis inhibitor as claimed in claim 8 which leads to reduced serum alanine-lactate aminotransferase activity relative to the serum alanine-lactate aminotransferase activity resulting from the use of the shark cartilage not subjected to the extraction step.

11. A composition containing a therapeutically effective amount of an angiogenesis inhibitor as claimed in claim 8 together with an acceptable carrier.

12. A method of inhibiting angiogenesis in an animal comprising administering to the animal an effective amount of an angiogenesis inhibitor as claimed in claim 8.

* * * * *